(12) United States Patent
Mikkelsen et al.

(10) Patent No.: US 7,860,355 B2
(45) Date of Patent: Dec. 28, 2010

(54) ATR-PROBE

(75) Inventors: Hakon Mikkelsen, Aldenhoven (DE); Andreas Müller, Ostfilden (DE); Patric Henzi, Karlsruhe (DE)

(73) Assignee: Endress +Hauser Conducta Gesellschaft fur Mess- und Regeltechnik mbH + co. KG, Gerlingen (DE)

( * ) Notice: Subject to any disclaimer, the term of this patent is extended or adjusted under 35 U.S.C. 154(b) by 0 days.

(21) Appl. No.: 12/382,595

(22) Filed: Mar. 19, 2009

(65) Prior Publication Data

US 2009/0263070 A1    Oct. 22, 2009

(30) Foreign Application Priority Data

Mar. 19, 2008   (DE) .................. 10 2008 015 065

(51) Int. Cl.
*G02B 6/00* (2006.01)
(52) U.S. Cl. .......................... 385/12; 385/13
(58) Field of Classification Search ............ 385/12, 385/13
See application file for complete search history.

(56) References Cited

U.S. PATENT DOCUMENTS

| | | | |
|---|---|---|---|
| 3,332,315 A * | 7/1967 | Wilks, Jr. ................. | 356/319 |
| 4,730,882 A * | 3/1988 | Messerschmidt ............ | 385/146 |
| 4,826,313 A * | 5/1989 | Schar et al. ................. | 356/51 |
| 5,703,366 A | 12/1997 | Sting | |

FOREIGN PATENT DOCUMENTS

| DE | 41 24 920 A1 | 2/1992 |
|---|---|---|
| DE | 42 28 070 A1 | 3/1994 |
| DE | 10 2006 036 409 A1 | 10/2007 |
| EP | 0 516 481 A2 | 12/1992 |
| WO | WO 2005/124300 A1 | 12/2005 |

* cited by examiner

*Primary Examiner*—Kevin S Wood
(74) *Attorney, Agent, or Firm*—Bacon & Thomas, PLLC

(57) ABSTRACT

An ATR-probe including: a housing having a media opening; a radiation guiding body closing the media opening and having two planparallel surfaces, between which light can be guided by means of total reflection. A section of a first planparallel surface bordered by a sealing ring can be contacted through the media opening with a medium to be measured. Transmission light conductors and receiving light conductors in the housing, wherein light is guided from the transmission light conductors, through the radiation guiding body, into the receiving light conductors; and wherein adjoining the first planparallel surface are first and second deflection surfaces, on which, respectively, light coupled into the radiation guiding body and light to be coupled out are deflected by total reflection, so that the light can be guided between the planparallel surfaces by means of total reflection. The light is not collimated, and the effective area of the transmission light conductors is smaller than the effective area of the receiving light conductors.

15 Claims, 3 Drawing Sheets

ATR-PROBE

TECHNICAL FIELD

The present invention relates to an ATR-probe (Attenuated Total Reflection Probe) for examining aqueous or liquid media.

BACKGROUND DISCUSSION

ATR-probes include, usually, a radiation guiding body, in which light is guided by means of total reflection at a surface of the body, wherein the surface is contactable with the medium to be examined, whereby the evanescent field of the light interacts with the medium.

The radiation guiding body is usually arranged at a media opening of a probe housing, which it closes, and through which a surface of the radiation guiding body is contactable with the medium.

A probe includes, furthermore, a light source for coupling light into the radiation guiding body and a detector for transducing the light coupled out of the radiation guiding body into an electrical signal, as well as, should the application require, light conductors for conducting light from the light source to the radiation guiding body or from the latter to the detector.

A challenge for the design of these probes is presented by the in- and out-coupling of the light into and out of the radiation guiding body, for, in the ideal case, each ray should, on the one hand, undergo a number of total reflections at the bounding surface in contact with the medium, and, on the other hand, the construction should be simple. The simplest construction would be a planparallel plate, between whose planparallel surfaces the light can be multiply guided by means of further total reflections. Here, however, there is the problem of the in-coupling. Diamond is the most suitable material for the radiation guiding body. Due to the high material price, however, complex optical designs, which consume a large volume of material, or require many facets, are too expensive.

Sting and Milosevic disclose, therefore, in U.S. Pat. No. 5,703,366 an ATR-probe, wherein a coupling body, for example, of ZnSe, sapphire or the like, and having an annular coupling surface, is placed on the radiation guiding body, so that a direct transferring of the light between ZnSe and diamond of the radiation guiding body is accomplished. The coupling body has inclined deflection surfaces, which enable it to couple the light at such angles into the radiation guiding body that, on the bounding surface facing away from the radiation guiding body and facing the medium, total reflection is brought about. In order to enable multiple reflections between the planparallel surfaces of the radiation guiding body, the coupling body has in its center a cavity surrounded by the annular coupling surface, so that light rays totally reflected from the media-contacting bounding surface cannot be coupled out in the region of the cavity, but are, instead, totally reflected anew to the media-contacting bounding surface. This construction is, however, very complicated, since the interface between the coupling body and the radiation guiding body is susceptible to disturbances, for example, on the basis of pressure- and temperature fluctuations, which can strongly degrade the effectiveness of the coupling.

German Patent, DE 10 2006 036 409 F1 discloses an ATR-probe, which eliminates the above problem, using a radiation guiding body having planparallel surfaces, which has, on the outer edges of the surfaces, pairwise oppositely lying, facet-like deflection surfaces, wherein light coupled in essentially perpendicularly to the surfaces at a first facet is deflected in such a manner that it, after a total reflection about in the center of the media-contacting surface, hits the second facet and is there deflected anew, in order then to be coupled out essentially perpendicularly to the planparallel surfaces of the radiation guiding body.

Although this approach quite easily achieves the desired simplicity of construction and the desired insensitivity, it is, nevertheless, achieved with a smaller sensitivity of the ATR-probe, for the ray undergoes only one reflection at a comparatively large angle on the media-contacting, bounding surface, so that the interaction of the evanescent field with the medium, which lastly determines the sensitivity of the probe, is comparatively slight.

SUMMARY OF THE INVENTION

It is, therefore, an object of the present invention to provide an ATR-probe, which overcomes the disadvantages of the state of the art.

The object is achieved according to the invention by the ATR-probe which includes: a housing having an inner space, which has a media opening to the outside of the housing, wherein the media opening is surrounded by an annular sealing surface; a transparent radiation guiding body closing the media opening and having two planparallel surfaces, between which light can be guided by means of total reflection, wherein at least one sensitive section of a first of the planparallel surfaces is positioned aligned with the media opening and is contactable through the media opening by a medium to be measured, wherein the sensitive section of the first surface is bordered by a sealing ring, which is arranged between the first surface and the sealing surface, wherein the radiation guiding body is supported with a support body extending out of the inner space; transmission light conductors, which extend in the inner space of the housing; receiving light conductors, which extend in the inner space of the housing; wherein light from the transmission light conductors can be coupled into the radiation guiding body from the side of the radiation guiding body facing away from the sensitive section, wherein there adjoins the first planparallel surface a first inclined deflection surface, on which light coupled into the radiation guiding body is deflected by total reflection in such a manner, that it first hits the second of the planparallel surfaces, and can then be guided in the radiation guiding body between the planparallel surfaces by means of further total reflections, wherein there adjoins the first surface opposite the first inclined deflection surface, furthermore, a second inclined deflection surface, on which light conveyed between the planparallel surfaces by means of total reflection impinges and is deflected by total reflection in such a manner, that it then is coupled out of the radiation guiding body on the side of the radiation guiding body facing away from the sensitive section and can be coupled into the receiving light conductors, wherein the first and the second deflection surfaces are arranged in the inner space of the housing outside of the region surrounded by the sealing ring, wherein the coupled light is not collimated, and wherein the effective area of the transmission light conductors, from which light is coupled into the radiation guiding body, is smaller than the effective area of the receiving light conductors, into which light is coupled from the radiation guiding body.

The effective area of the transmission light conductors refers, especially, to the sum of the end face areas of a plurality of transmission light conductors, from which light can be coupled.

The effective area of the receiving light conductors refers, especially, to the sum of the end face areas of a plurality of receiving light conductors, into which light can be coupled.

In a further development of the invention, the first inclined surface and the transmission light conductors are positioned and oriented in such a manner, that, at most, a negligible fraction F1 of the in-coupled light intensity hits an area of the first surface, against which the sealing ring lies, before the first total reflection on the second surface or directly after the first total reflection on the second surface, wherein F1<0.2, preferably <0.1 and especially preferably <0.05.

Preferably, furthermore, the second inclined surface and the receiving light conductors are positioned and oriented in such a manner, that, at most, a negligible fraction F2 of the light intensity out-coupled into the receiving light conductors hits an area of the first surface, against which the sealing ring lies, after the last total reflection on the second surface or directly before the last total reflection on the second surface, wherein F2<0.3, preferably <0.2 and especially preferably <0.1.

The support body can, according to a currently preferred embodiment of the invention, include a ferrule, in which end sections of the light conductors are guided, in order to position and to orient the light conductors with respect to the radiation guiding body.

Between the end faces of the light conductors and the second surface of the radiation guiding body, according to a further development, a separation of at least 20 μm, preferably at least 60 μm, and especially preferably at least 100 μm is provided.

Preferably, the end faces of the light conductors are not oriented exactly parallel to the second surface, whereby interferences between the end faces and the second surface are prevented or reduced.

The separation can be set, for example, via a spacing body, which is arranged between the support body and the radiation guiding body.

In an embodiment of the invention, the spacing body includes a rough surface on its side facing the radiation guiding body, at least in a region, especially a central region, of the second surface of the radiation guiding body. The surface should, in such case, be sufficiently rough, that the light is, at most, negligibly coupled from the radiation guiding body and into the space holder, or reflected on the surface of the space holder. Otherwise, by undesired multiple reflections between the radiation guiding body and the space holder, a kind of interferometer would arise. The space holder can include, for example, a roughened polymer film, for example, Kapton film.

In another embodiment of the invention, the support body includes, on its surface facing the radiation guiding body, protrusions, with which the separation between the second surface of the radiation guiding body and the end faces of the light conductors is defined.

In a currently preferred embodiment of the invention, the radiation guiding body is monolithic and comprises diamond, sapphire or ZnSe.

The transmission light conductors and the receiving light conductors comprise, preferably, silver halide fibers or chalcogenide fibers.

To the extent that the ATR-probe should serve as a spectrometer, a dispersive element is provided, which can include, for example, a graduated filter. Equally, gratings are suitable. Instead of a dispersive element, likewise an interferometer can be provided.

In a currently preferred embodiment of the invention, the second surface extends to the outer edge of the radiation guiding body, i.e., the second surface overlaps the first and the second deflection surfaces.

In another embodiment of the invention, there adjoins the second surface, at least sectionally aligned with the first inclined deflection surface, a first refracting surface, which is inclined with respect to the second surface, and by which the in-coupled light is refracted. Correspondingly, a second refracting surface can be provided, which adjoins the second surface opposite the first refracting surface and is arranged at least sectionally aligned with the second inclined deflection surface, and by which the light to be out-coupled is refracted.

BRIEF DESCRIPTION OF THE DRAWINGS

The invention will now be explained on the basis of examples of embodiments presented in the drawing, the figures of which show as follows.

DETAILED DISCUSSION

Figure 1:
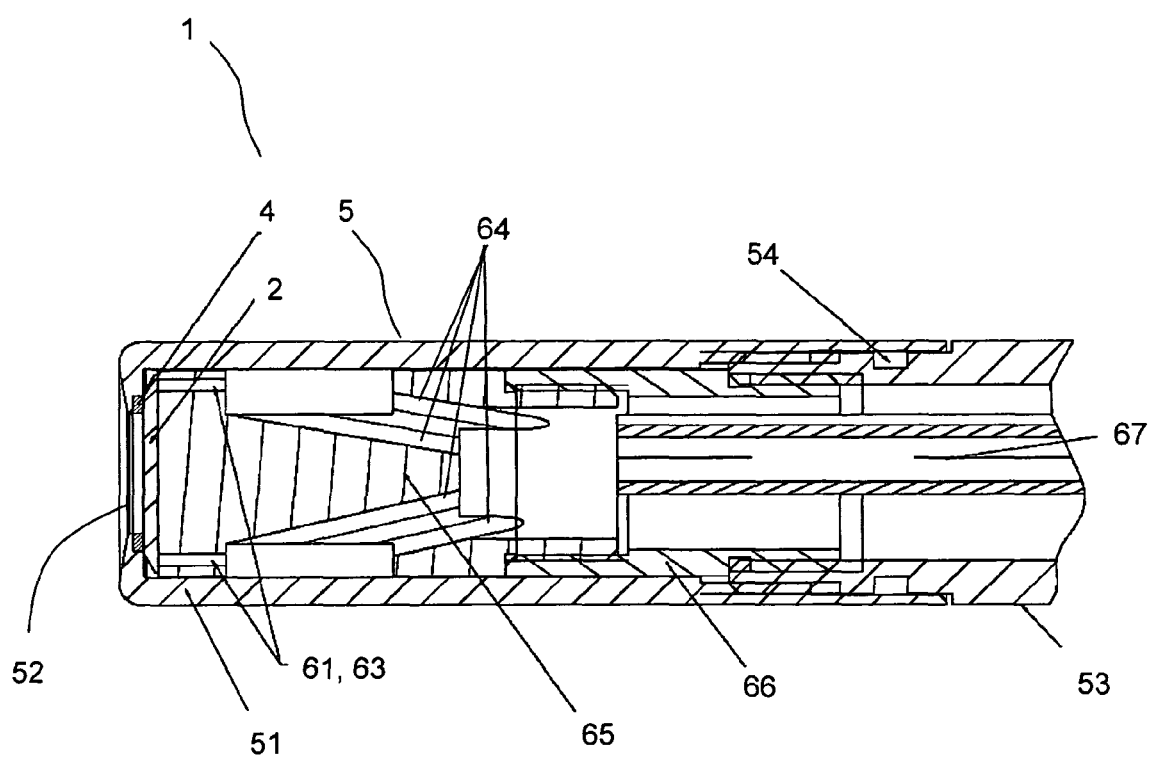
FIG. 1 a sectional drawing of an ATR-probe of the invention with a radiation guiding body having planparallel surfaces.

Construction of an ATR-probe of the invention is presented in longitudinal section in FIG. 1. Provided as radiation guiding body 2 is a diamond-element having planparallel surfaces. Radiation guiding body 2 is axially held, with interpositioning of an elastic sealing ring 4 (especially in the form a gasket), against a peripheral sealing surface around a frontal opening 52 in a cylindrical probe housing 5. Through the frontal opening 52, a section of a first planparallel surface of the radiation guiding body 2 can be contacted with a medium to be measured. The sealing ring 4 can comprise, in principle, any media resistant (especially relative to acids, bases and solvents), as well as pressure- and temperature-resistant materials. Currently, Kalrez elastomer is preferred.

The probe housing includes a probe head 51, which has, on its frontal end face, the frontal opening 52. To the rear, the probe head is adjoined by a probe shaft tube 53, which engages in the probe head, wherein a sealing ring 54 is provided between the probe shaft tube 53 and the probe head.

Arranged in the probe head 51 is a fiber ferrule 6, with which light conductors are positioned. To this end, the ferrule 6 has adjusting bores 61, 63 in a front part 65 of the ferrule, in which the fibers are adhered by means of a suitable adhesive, for example, with an epoxide resin, which with the material of the light conductor fibers is compatible, wherein the light conductor fibers comprise, especially, silver halide or chalcogenide.

The fibers are not illustrated in the drawing, in order to avoid clutter. Basically, the end face of the front part 65 of the ferrule 6 can contact the radiation guiding body directly, wherein, however, it is to be heeded, that the end faces of the fibers should be spaced, preferably, sufficiently from the radiation guiding body, in order to prevent intensity modulations on the basis of Fabry-Perot interferences.

For this, either the end faces of the fibers can be set back with respect to the end face of the front part 65 of the ferrule 6, or a spacer can be provided between the front part 65 of the ferrule 6 and the radiation guiding body 2, when the end faces of the fibers are essentially flush with the end face of the front part of the ferrule.

The second alternative provided here is that wherein, in this connection, a polymer film, especially a polyimide-film, preferably Kapton, with a thickness of about 60 μm is clamped between the end face of the front part of the ferrule and the radiation guiding body.

The surface of the polymer film on the side facing the radiation guiding body is roughened with a roughness of a few μm, in order to assure, that the film does not degrade the signal of the ATR-probe.

For the case in which the end face of the front part 65 of the ferrule lies directly against the radiation guiding body, the end face is to be roughened appropriately in its central region, in order sufficiently to reduce interaction with the totally reflected light in the radiation guiding body.

The front part of the ferrule includes, furthermore, light conductors canals 64, which are manufactured with greater tolerances than the adjusting bores 61, 63, and through which the light conductors are guided to the adjusting bores.

Adjoining the rear-side of the front part 65 of the ferrule is a posterior part 66, which is supported axially on the probe shaft tube 53, and, thus, clamps the front part 65 of the ferrule 6 against the radiation guiding body.

The ferrule can comprise, basically, any sufficiently formstable materials compatible with the material of the light conductors, or optical fibers, wherein, currently, PEEK is preferable, since it enables a simple and exact manufacture, is cost-effective and also has sufficient mechanical stability in the case of high temperatures.

In the posterior part 66 of the ferrule, which can comprise stainless steel, and which has an essentially cylindrically symmetrical construction, the probe-head-side, end section of a plastic tube 67 is arranged, in which the light conductors are guided through the probe shaft to the probe head. The plastic tube comprises PEEK in a currently preferred embodiment.

The radiation guiding body 2 can be manufactured, for example, of the materials, natural diamond, synthetically manufactured CVD-diamond, sapphire or ZnSe. Other optically transparent materials, which are, for the desired applications, sufficiently scratch-resistant, pressure-resistant and chemically resistant, can likewise be used.

The currently preferred diameter of the radiation guiding body amounts to not more than 10 mm, especially preferably about 9 mm, in order that the radiation guiding body can be integrated in a probe having an outer diameter of about 12 mm. The material thickness of the radiation guiding body can be, especially, 0.5 mm to 1.0 mm, wherein, currently, 0.6 mm is preferable.

Figure 2:
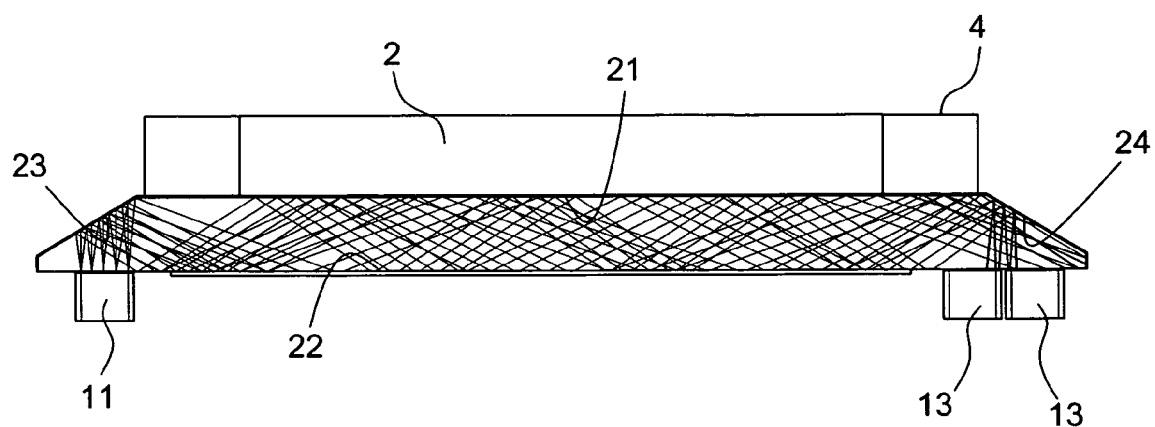
FIG. 2 a sectional drawing through a radiation guiding body having planparallel surfaces according to a first form of embodiment of the invention, including drawn, computer-ascertained, ray paths through the radiation guiding body.

Details for the radiation guiding body will now be explained on the basis of FIGS. 2 and 3. The example of an embodiment illustrated in FIG. 2 shows a radiation guiding body 2 of diamond having a first surface 21 and a thereto parallel, second surface 22, wherein the two surfaces are planparallel. Lying against the first surface is an annular gasket 4. The region of the first surface surrounded by the gasket is, in measurement operation contactable by a medium to be examined. Outwards from the gasket 4, the radiation guiding body has two oppositely lying facets 23 and 24 adjoining the first surface 21, wherein a first of the facets, facet 23, serves as first deflection surface, on which light radiated in through the second surface 22 is totally reflected. Following a plurality of total reflections between the first surface 21 and the second surface 22, the part of the light, which hits the second facet 24, which serves as second deflection surface, is totally reflected, so that it hits the second surface 22 at such an angle that it can be out-coupled.

For MIR applications a facet angle of less than 42° is required. A minimal value for the facet angles is 15°. Preferably, the facet angle should be less than 35°, wherein currently 30° to 33° is preferred. In the presented form of embodiment, the facet angle amounts to 31.5°. The angles of the first and second facets can, basically, be unequal, while, in the presented examples of embodiments, the facet angles are equal, within manufacturing tolerances.

Figure 3:
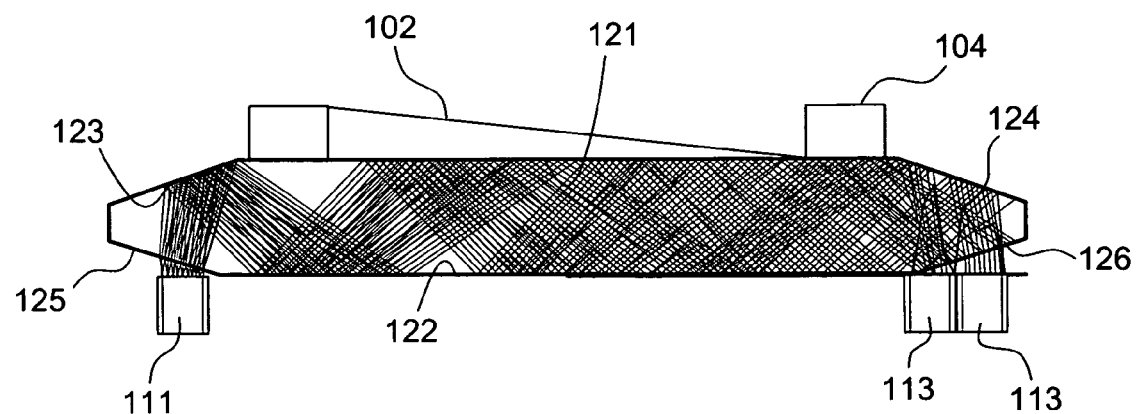
FIG. 3 a sectional drawing through a radiation guiding body having planparallel surfaces according to a second form of embodiment of the invention, including drawn, computer-ascertained, ray paths through the radiation guiding body.

In the case of the second example of an embodiment according to FIG. 3, the radiation guiding body has, in turn, two planparallel surfaces 121 and 122, wherein the first of the surfaces 121 can be contacted with a medium to be measured in a region surrounded by a sealing ring 104, and wherein light is coupled into the radiation guiding body 102 from the side of the second surface 122.

In the case of this example of an embodiment, the radiation guiding body is likewise comprised of diamond, wherein it has four facets, of which a first facet 123 and a second facet 124 adjoin the edge of the first surface 121 and again serve as first and second deflection surfaces for total reflection of the in- and out-coupled light, respectively.

Furthermore, the radiation guiding body 102 has a third facet 125 and a fourth facet 126, which adjoin the second surface, lie opposite to one another and align, at least sectionally, with the first and second facets, respectively. The third facet 125 serves as first refracting surface, through which light is coupled into the radiation body and is refracted, before it hits the first facet, so that the K-vector of the light after the refraction has a component in the direction of a middle plane of the radiation guiding body, which extends parallel to the lines of intersection between the planparallel surfaces and the facets.

The fourth facet 126 serves as second refracting surface, on which light to be coupled out hits, which is totally reflected by the second facet 124, and which, during the out-coupling, is refracted in such a manner, that a component of the K-vector of the light directed away from the middle plane of the radiation guiding body is reduced after the refraction.

The sum of the four facet angles of the radiation guiding body having planparallel surfaces amounts preferably to not more than 120°.

In the present embodiment, all facet angles are essentially equal, namely 19°. Nevertheless, the facets can be sized differently, such as is evident in FIG. 3. The third and fourth facets start at a greater distance from the middle plane than the first and second facets.

In another embodiment, the first and the second facets have a first angle, and the third and fourth facets a second angle, which is different from the first angle.

Finally, all facets can have different angles.

With reference to FIGS. 2 and 3, now the arrangement of the transmission light conductors 11; 111 or receiving light conductors 13; 113 and the, in each case, resulting ray paths will be explained.

The light conductors are oriented by means of the adjusting bores (not shown in FIGS. 2 and 3) essentially perpendicularly to the planparallel surfaces.

The light conductors 11, 13, 111, 113 have a typical numerical aperture lying, for example, in the range of 0.2 to 0.5. In the case NA=0.25, the light ray diverges thereby to a light beam of about +/−14° beam angle in air. Through the high index of refraction of the radiation guiding body 2, 102, the maximum beam angle of the light beam in the radiation guiding body 2, 102 becomes smaller again upon entry. In spite of this, the beam expands, due to the high NA and the many total reflections in the radiation guiding body 2, 102, toward the second facet 24, 124, where therebeneath the receiving light conductors 13, 113 are located. In order to register more light for the detector, the ATR-probe has more receiving light conductors 13, 113 than transmission light conductors 11, 111.

An important requirement for the ATR process probe is that the sealing ring 4, 104 on the radiation guiding body 2, 102 must have an as small as possible, preferably no, influence on the spectrum of the process probe. Therefrom there results, that the light rays, which are to be coupled out to the receiving light conductors 13; 113, must not be, or, at most, negligibly totally reflected in the region of the first surface 21, 121, against which the sealing ring 4, 104 lies.

The optics design with the transmission and receiving light conductors 11, 13, 111, 113, the radiation guiding body 2, 102 and the sealing ring 4, 104 includes, in this respect, the symmetry described in the following with respect to the radiation guidance.

Through a suitable choice of the facet angle, the thickness of the radiation guiding body 2, 102, the position of the transmission light conductors 11, 111 and the inner and outer diameters of the sealing ring 4, 104, based on the given NA of the transmission light conductors 11, 111, no light rays hit the underside of the sealing ring 4, 104 in the vicinity of the transmission light conductors 11, 111.

After the second total reflection, which occurs on the second surface 22, 122 of the radiation guiding body 2, 102, the angles of reflection of the individual, calculated rays do not change, and therewith also not the angular content of the bundle of rays, because the radiation guiding body 2, 102 is a planparallel plate in its central region. The light rays, which impinge from below on the lower side of the sealing ring 4, 104 in the vicinity of the receiving light conductors 13, 113, have exactly such angular content, and can, therefore, not follow the ray path via the second facet 24, 124 to the receiving light conductors 13, 113. This can be easily seen from FIGS. 2 and 3.

The end faces of the light conductors have, in the first example of an embodiment, a separation of about 60 μm from the second surface 22 of the radiation guiding body 2, in order, especially, to prevent pressure-dependent interferences. This distance is set by a polyimide film (Kapton) of corresponding thickness indicated in FIG. 1 as a reinforced line. The film is clamped between the ferrule and the radiation guiding body. For preventing disturbances of the signal by the film, the film is roughened.

Figure 4:
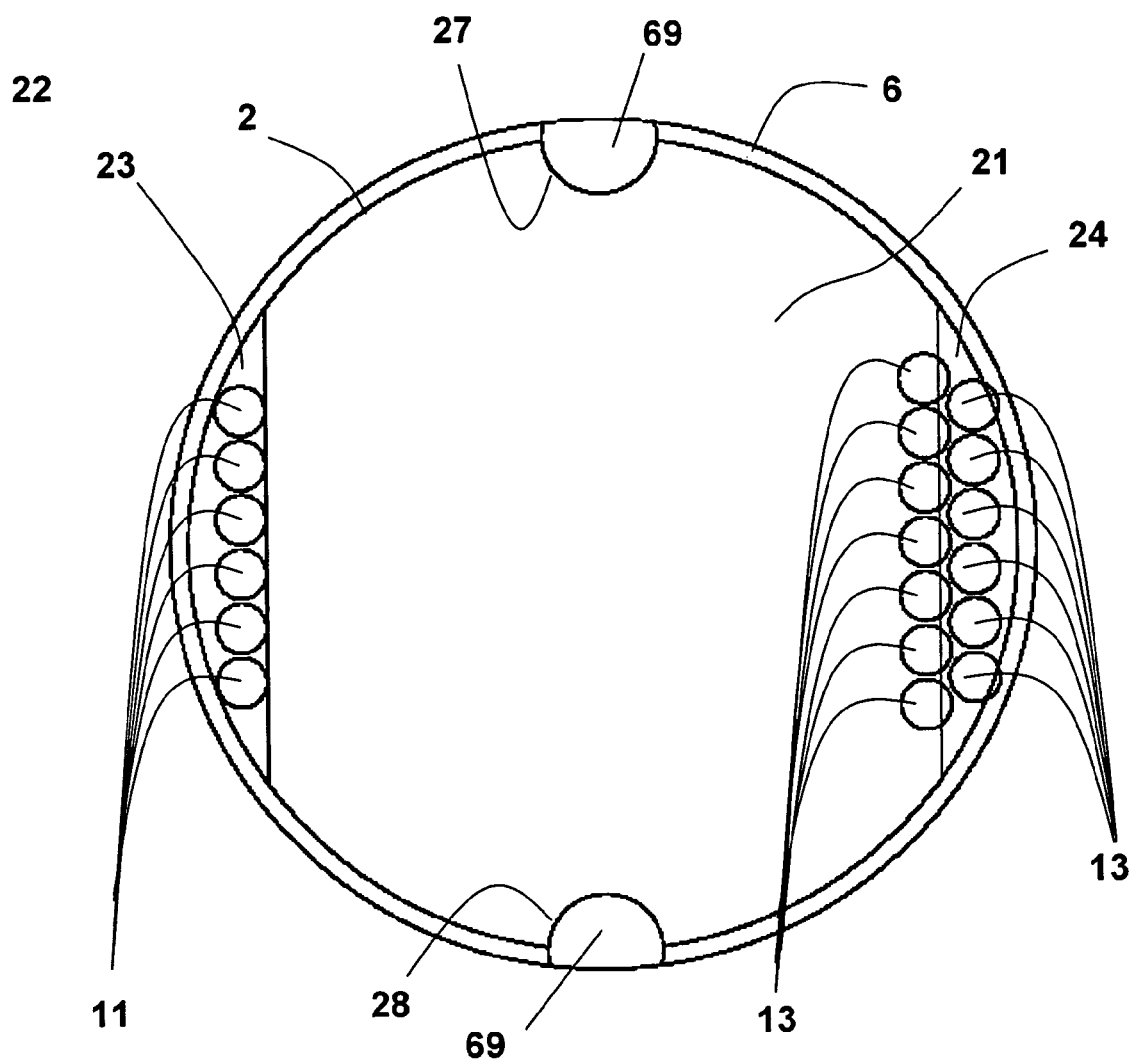
FIG. 4 a plan view of an end face a fiber ferrule for positioning under a radiation guiding body according to a form of embodiment of the invention.

FIG. 4 shows a plan view of the end face of the ferrule 6, with the light conductors 11 and 13, in individually associated, adjusting bores, as well as the superimposed radiation guiding body 2. The intersections between the facets 23, 24 and the first surface 21 are clearly indicated.

The radiation guiding body 2 has, at locations about 90° from the facets, first and second securement bores 27, 28, in which posts 69 engage, which protrude from the end face of the ferrule, in order to assure correct positioning of the facets 23, 24 with respect to the light conductors 11, 13.

The invention claimed is:

1. An ATR-probe, comprising:
  a housing having an inner space with a media opening opening to outside of said housing, wherein said media opening is surrounded by an annular sealing surface;
  a transparent radiation guiding body closing said media opening and having two planparallel surfaces, between which light can be guided by means of total reflection, at least one sensitive section of a first surface of said planparallel surfaces is positioned in alignment with said media opening and can be contacted through said media opening with a medium to be measured, wherein said at least one sensitive section of said first surface is bordered by a sealing ring, which is arranged between said first surface and said sealing surface, wherein said transparent radiation guiding body is supported from said inner space by a support body;
  transmission light conductors, which extend in said inner space of said housing; and
  receiving light conductors, which extend in said inner space of said housing, wherein:
  light from said transmission light conductors can be coupled into said transparent radiation guiding body from the side of said transparent radiation guiding body facing away from said at least one sensitive section;
  adjoining said surface of said first planparallel surfaces, a first inclined deflection surface is provided, on which light coupled into said transparent radiation guiding body is deflected by total reflection in such a manner, that it hits first on a second surface of said planparallel surfaces, and can be guided in said radiation guiding body between said two planparallel surfaces by means of further total reflections; adjoining said first surface, opposite to said first inclined deflection surface, a second inclined deflection surface is provided, on which light guided between said two planparallel surfaces by means of total reflection impinges and is deflected by total reflection in such a manner, that it can then, on the side of said transparent radiation guiding body facing away from said at least one sensitive section, be coupled out of said transparent radiation guiding body and into said receiving light conductors; said first and said second inclined deflection surfaces are arranged in said inner space of said housing outside of the region surrounded by said sealing ring;
  the coupled light is not collimated; and
  the effective area of said transmission light conductors, from which light is coupled into said transparent radiation guiding body, is smaller than the effective area of said receiving light conductors, into which light from said transparent radiation guiding body is coupled.

2. The ATR-probe as claimed in claim 1, further comprises:
a support body comprises a ferrule, in which end sections of said light conductors are guided, in order to position and to orient said light conductors with respect to said transparent radiation guiding body.

3. The ATR-probe as claimed in claim 1, wherein:
between end faces of said light conductors and said second surface of said transparent radiation guiding body, a separation of at least 20 μm, preferably at least 60 μm, and especially preferably at least 100 μm is provided.

4. The ATR-probe as claimed in claim 3, wherein:
the separation is set via a spacing body, which is arranged between said support body and said transparent radiation guiding body.

5. The ATR-probe as claimed in claim 4, wherein:
said spacing body has a rough surface on its side facing said transparent radiation guiding body.

6. The ATR-probe as claimed in claim 3, wherein:
said support body has on its surface facing said transparent radiation guiding body protrusions, with which the separation between said second surface of said transparent radiation guiding body and said end faces of said light conductors is defined.

7. The ATR-probe as claimed in claim 1, wherein:
said transparent radiation guiding body is monolithic and comprises diamond, sapphire or ZnSe.

8. The ATR-probe as claimed in claim 1, wherein:
said transmission light conductors and said receiving light conductors include silver halide fibers or chalcogenide fibers.

9. The ATR-probe as claimed in claim 1, further comprising:
a dispersive element, which includes, for example, a graduated filter, a grating or an interferometer.

10. The ATR-probe as claimed in claim 1, wherein:
said second surface extends to the outer edge of said transparent radiation guiding body, so that said second surface overlaps with said first and said second deflection surfaces.

11. The ATR-probe as claimed in claim 1, wherein:
adjoining said second surface and at least partially aligned with said first inclined deflection surface is a first refracting surface, which is inclined with respect to said second surface, and by which in-coupled light is refracted.

12. The ATR-probe as claimed in claim 11, further comprising:
a second refracting surface, which adjoins said second surface opposite to said first refracting surface, and which is arranged at least sectionally aligned with said second inclined deflection surface, and by which light to be out-coupled is refracted.

13. An ATR-probe, comprising:
a housing having an inner space with a media opening opening to outside of said housing, wherein said media opening is surrounded by an annular sealing surface;
a transparent radiation guiding body closing said media opening and having two planparallel surfaces, between which light can be guided by means of total reflection, at least one sensitive section of a first surface of said planparallel surfaces is positioned in alignment with said media opening and can be contacted through said media opening with a medium to be measured, wherein said at least one sensitive section of said first surface is bordered by a sealing ring, which is arranged between said first surface and said sealing surface, wherein said transparent radiation guiding body is supported from said inner space by a support body;
transmission light conductors, which extend in said inner space of said housing; and
receiving light conductors, which extend in said inner space of said housing, wherein:
light from said transmission light conductors can be coupled into said transparent radiation guiding body from the side of said transparent radiation guiding body facing away from said at least one sensitive section;
adjoining said surface of said first planparallel surfaces, a first inclined deflection surface is provided, on which light coupled into said transparent radiation guiding body is deflected by total reflection in such a manner, that it hits first on a second surface of said planparallel surfaces, and can be guided in said radiation guiding body between said two planparallel surfaces by means of further total reflections; adjoining said first surface, opposite to said first inclined deflection surface, a second inclined deflection surface is provided, on which light guided between said two planparallel surfaces by means of total reflection impinges and is deflected by total reflection in such a manner, that it can then, on the side of said transparent radiation guiding body facing away from said at least one sensitive section, be coupled out of said transparent radiation guiding body and into said receiving light conductors; said first and said second inclined deflection surfaces are arranged in said inner space of said housing outside of the region surrounded by said sealing ring;
the coupled light is not collimated;
the effective area of said transmission light conductors, from which light is coupled into said transparent radiation guiding body, is smaller than the effective area of said receiving light conductors, into which light from said transparent radiation guiding body is coupled; and
said first inclined surface and said transmission light conductors are positioned and oriented in such a manner that, at most, a negligible fraction F1 of the in-coupled light intensity hits an area of said first inclined surface, against which said sealing ring lies, before the first total reflection on said second surface or directly after the first total reflection on said second surface, wherein F1<0.2.

14. An ATR-probe, comprising:
a housing having an inner space with a media opening opening to outside of said housing, wherein said media opening is surrounded by an annular sealing surface;
a transparent radiation guiding body closing said media opening and having two planparallel surfaces, between which light can be guided by means of total reflection, at least one sensitive section of a first surface of said planparallel surfaces is positioned in alignment with said media opening and can be contacted through said media opening with a medium to be measured, wherein said at least one sensitive section of said first surface is bordered by a sealing ring, which is arranged between said first surface and said sealing surface, wherein said transparent radiation guiding body is supported from said inner space by a support body;
transmission light conductors, which extend in said inner space of said housing; and
receiving light conductors, which extend in said inner space of said housing, wherein:
light from said transmission light conductors can be coupled into said transparent radiation guiding body from the side of said transparent radiation guiding body facing away from said at least one sensitive section;
adjoining said surface of said first planparallel surfaces, a first inclined deflection surface is provided, on which light coupled into said transparent radiation guiding body is deflected by total reflection in such a manner, that it hits first on a second surface of said planparallel surfaces, and can be guided in said radiation guiding body between said two planparallel surfaces by means of further total reflections; adjoining said first surface, opposite to said first inclined deflection surface, a second inclined deflection surface is provided, on which light guided between said two planparallel surfaces by means of total reflection impinges and is deflected by total reflection in such a manner, that it can then, on the side of said transparent radiation guiding body facing away from said at least one sensitive section, be coupled out of said transparent radiation guiding body and into said receiving light conductors; said first and said second inclined deflection surfaces are arranged in said inner space of said housing outside of the region surrounded by said sealing ring;
the coupled light is not collimated;

the effective area of said transmission light conductors, from which light is coupled into said transparent radiation guiding body, is smaller than the effective area of said receiving light conductors, into which light from said transparent radiation guiding body is coupled; and said second inclined surface and said receiving light conductors are positioned and oriented in such a manner that, at most, a negligible fraction F2 of the light intensity coupled out into said receiving light conductors hits an area of said first surface, against which said sealing ring lies, after the last total reflection on said second surface or directly before the last total reflection on said second surface, wherein F2<0.3.

15. An ATR-probe, comprising:

a housing having an inner space with a media opening opening to outside of said housing, wherein said media opening is surrounded by an annular sealing surface;

a transparent radiation guiding body closing said media opening and having two planparallel surfaces, between which light can be guided by means of total reflection, at least one sensitive section of a first surface of said planparallel surfaces is positioned in alignment with said media opening and can be contacted through said media opening with a medium to be measured, wherein said at least one sensitive section of said first surface is bordered by a sealing ring, which is arranged between said first surface and said sealing surface, wherein said transparent radiation guiding body is supported from said inner space by a support body;

transmission light conductors, which extend in said inner space of said housing; and receiving light conductors, which extend in said inner space of said housing, wherein:

light from said transmission light conductors can be coupled into said transparent radiation guiding body from the side of said transparent radiation guiding body facing away from said at least one sensitive section;

adjoining said surface of said first planparallel surfaces, a first inclined deflection surface is provided, on which light coupled into said transparent radiation guiding body is deflected by total reflection in such a manner, that it hits first on a second surface of said planparallel surfaces, and can be guided in said radiation guiding body between said two planparallel surfaces by means of further total reflections; adjoining said first surface, opposite to said first inclined deflection surface, a second inclined deflection surface is provided, on which light guided between said two planparallel surfaces by means of total reflection impinges and is deflected by total reflection in such a manner, that it can then, on the side of said transparent radiation guiding body facing away from said at least one sensitive section, be coupled out of said transparent radiation guiding body and into said receiving light conductors; said first and said second inclined deflection surfaces are arranged in said inner space of said housing outside of the region surrounded by said sealing ring;

the coupled light is not collimated;

the effective area of said transmission light conductors, from which light is coupled into said transparent radiation guiding body, is smaller than the effective area of said receiving light conductors, into which light from said transparent radiation guiding body is coupled;

said first inclined surface and said transmission light conductors are positioned and oriented in such a manner that, at most, a negligible fraction F1 of the in-coupled light intensity hits an area of said first inclined surface, against which said sealing ring lies, before the first total reflection on said second surface or directly after the first total reflection on said second surface, wherein F1<0.2, and said second inclined surface and said receiving light conductors are positioned and oriented in such a manner that, at most, a negligible fraction F2 of the light intensity coupled out into said receiving light conductors hits an area of said first surface, against which said sealing ring lies, after the last total reflection on said second surface or directly before the last total reflection on said second surface, wherein F2<0.3.

* * * * *